United States Patent [19]

Mehta et al.

[11] Patent Number: 5,173,399
[45] Date of Patent: *Dec. 22, 1992

[54] MOUSE MONOCLONAL ANTIBODIES TO HIV-1P24 AND THEIR USE IN DIAGNOSTIC TESTS

[75] Inventors: Smriti U. Mehta, Libertyville; Jeffrey C. Hunt, Lindenhurst; Sushil G. Devare, Northbrook, all of Ill.

[73] Assignee: Abbott Laboratories, Abbott Park, Ill.

[*] Notice: The portion of the term of this patent subsequent to Jan. 8, 2008 has been disclaimed.

[21] Appl. No.: 204,798

[22] Filed: Jun. 10, 1988

[51] Int. Cl.$^5$ .................. C12Q 1/70; G01N 33/53; C12N 5/20; C07K 15/28

[52] U.S. Cl. .......................... 435/5; 435/71; 435/792; 435/793; 435/794; 435/795; 435/971; 435/974; 435/975; 435/240.27; 530/388.3; 436/548

[58] Field of Search ............... 435/5, 7.1, 7.92–7.95, 435/971, 974, 975, 240.27; 530/387; 436/548

[56] References Cited

U.S. PATENT DOCUMENTS 4,376,110  3/1983  David et al. ................. 436/513
4,755,457  7/1988  Guroff et al. ................. 435/5

OTHER PUBLICATIONS

Grunow et al., "The high efficiency, human Bcell immortalizing heteromycloma CB-F7", J. Immunol. Meth. 106(1988), 257–265.
Niedrig et al., "Monoclonal Antibodies Directed against Human Immunodeficiency Virus (HIV) gag Proteins with Specificity for Conserved Epitopis in HIV-1, HIV-2 and Human Immunodeficiency Virus", J. Gen. Virol., 69(1988), 2109–2114.
Higgins et al., "Detection and Differentiation by Sandwich Enzyme-Linked Immunosorbent Assay of Human T-Cell Lymphotropic Virus Type III/Lymphadenopathy-Associated Virus-and Acquired Immunodeficiency Syndrome-Associated Retrovirus like Clinical Isolates", J. Clin. Microbiol., vol. 24, (1986) 424–430.
Caruso et al., "Liquid competition radioimmunoassay for the detection and quantitation of the HIV p. 24", J. Virol. Meth., 17(1987) 199–210.
Evans et al., "Human Monoclonal antibody Directed Against gag Gene Products of the Human Immunodeficiency Virus", J. Immunol., 140 (1988) 941–3.
Hattori et al., "Characterization of Three Monoclonal Antibodies (VAK3-5) That Identify p24, Core Protein of Human Immunodeficiency Virus and Its Precursors", Jpn. J. Cancer Res. (Gann) 78(Mar. 1987) 235–41.
di Marzo Veronese et al., "Moncolonal Antibodies specific for p24, the major core protein of human T-cell leukemia virus type III", Proc. Natl. Acad. Sci., USA, 82(1985) 5199–5202.
Kanki et al., "Serologic Identification and Characterization of a Macaque T-Lymphotropic Retrovirus Closely Related to HTLV-III", Science 228(1985) 1199–1201.
Ghrayeb et al., "Human T-Cell Lymphotropic Virus Type III (HTLV-III) Core Antigens: Synthesis in *Escherichia coli* and Immunoreactivity with Human Sera", DNA, 5(1986) 95–9.
Marcus-Sekura et al., "Reactivity of an HIV gag gene polypeptide expressed in *E. coli* with sera from AIDS patients and monoclonal antibodies to gag", Biochem. Biophys. Acta 949 Feb. 28, 1988 213–23.
Ferns et al., "Characterization of Monoclonal Antibodies Against the Human Immunodeficiency virus (HIV) gag Products and Their Use in Monitoring HIV Isolate Variation", J. Gen. Virol., 68(1987) 1543–51.

*Primary Examiner*—Christine M. Nucker
*Assistant Examiner*—M. P. Woodward
*Attorney, Agent, or Firm*—Priscilla E. Porembski; Joan D. Eggert

[57] ABSTRACT

The present invention provides monoclonal antibodies demonstrating specific reactivity with HIV-1 p24. One monoclonal antibody designated 31-42-19 recognizes an unique epitope on HIV-1 p24 that is not immunogenic in humans. 31-42-19 also reacts with an antigenically cross reactive epitope on HIV-2 p24. Another monoclonal antibody designated 31-90-25 recognizes an epitope within a highly immunogenic region of HIV-1 p24. The present invention also provides cell lines capable of producing these monoclonal antibodies. The invention also includes a highly sensitive enzyme immunoassay for the detection of HIV-1 p24 in biological fluids, using a monoclonal antibody mixture. The present invention further provides methods for the use of these monoclonal antibodies for the detection of anti-HIV-1 p24 antibodies and HIV-2 p24 antigen in biological samples.

21 Claims, 4 Drawing Sheets

MOUSE MONOCLONAL ANTIBODIES TO HIV-1P24 AND THEIR USE IN DIAGNOSTIC TESTS

BACKGROUND OF THE INVENTION

The present invention relates to the detection of the Human Immunodeficiency Virus (HIV-I), the etiologic agent of Acquired Immunodeficiency Syndrome (AIDS), in serum, plasma or other body fluids. In particular, this invention describes a diagnostic test which employs a combination of unique mouse monoclonal antibodies as a probe for the detection of HIV-I core protein p24.

AIDS is an infectious and fatal disease transmitted through intimate sexual contact and exposure to contaminated blood or blood products. HIV-I includes the formerly named viruses Human T-cell Lymphotrophic Virus Type III (HTLV III), Lymphadenopathy Associated Virus (LAV) and AIDS Associated Retrovirus (ARV). HIV-I is related to a group of cytopathic retroviruses, namely lentiviruses, on the basis of in vitro characteristics, morphologic features and nucleotide sequences (Gonda et al., Science (1985) 227:177–179; Stephan et al., Science (1986) 231:589–594).

Presently, the most reliable method for the diagnosis of AIDS is testing for serum antibodies to HIV-I structural proteins. Although these tests are highly sensitive, the presence of antibodies in blood only indicates prior exposure to HIV-I and not the presence of infection with HIV-I. In addition, once a primary infection is established, a time interval of up to 6-8 weeks may elapse before people infected with HIV-I seroconvert (Cooper et al., Lancet (1985) 1:537–540; Ho et al., Ann. Int. Med. (1985) 103:880–883). During this time, virus may be actively replicating in the host, thus making the host a seronegative source of infectious blood. Therefore, there is a need to detect virus infection during the time that precedes seroconversion in order to prevent the spread of infection through blood transfusions.

The most widely used methods for detecting HIV-I in infected individuals include the isolation of virus from infected blood or blood cells and subsequent in vitro propagation of the virus in lymphocyte cultures. In vitro replicating virus may be detected by measuring reverse transcriptase (RT) levels, immunocytochemical staining of viral proteins, electron microscopy, and nucleic acid probe hybridization. In vitro cultivation and isolation of virus are labor intensive, technique sensitive and may not be practical for use as a routine diagnostic method. Recently, enzyme immunoassays have been developed to detect HIV-I antigens in serum and other body fluids of infected people (Goudsmit et al., The Lancet (1986) 2:177–180; Allain et al., Brit. Med. J. (1986) 2993:1459–1462; Caruso et al., J. Virol. Methods (1987) 17:199–210). These enzyme immunoassays are easier to perform, specific for HIV-I, and more sensitive than conventional RT assays. Through the use of these assays, longitudinal studies carried out on high risk individuals have established a definite correlation between HIV-I antigenemia, the decline of antibodies to core protein p24, and disease progression from asymptomatic seropositivity to full blown AIDS. (Paul et al., J. Med. Virol. (1987) 22:357–363; Lange et al., Brit. Med. J. (1986) 293:1459–1462; Goudsmit et al., Concise Comm. (1986) 155:558–560; Lange et al., The Lancet (1987) Feburary: 190.) In addition, a significant decrease in the level of HIV-I p24 antigen has been observed in patients treated with AZT (Chaisson et al., New Eng. J. Med. (1986) 315:1610–1611). These studies demonstrate that HIV-I core antigens may be important serological markers for initial diagnosis of infection and disease progression, and as well may provide a tool for monitoring antiviral therapy in AIDS patients.

SUMMARY OF THE INVENTION

Mouse monoclonal antibodies to HIV-I p24 are provided by the invention which are highly specific reagents employed in immunoassays designed to detect and/or capture HIV-I p24. Available information on the nature and consequence of HIV-I infection establishes a need for the early detection of HIV-I antigens, especially p24, prior to seroconversion in people infected with HIV-I.

A highly sensitive diagnostic assay to detect HIV-I p24, using a mixture of two monoclonal antibodies as a probe, is provided by the present invention. One monoclonal antibody, 31-42-19, recognizes a unique epitope on HIV-I p24 which is not recognized by sera from seropositive individuals. In addition, monoclonal antibody 31-90-25, which recognizes an epitope within a highly immunogenic region of HIV-I p24, also is employed in the assay. These two monoclonals have been found to bind synergistically to HIV-I p24; that is, the binding of one monoclonal antibody enhances the binding of the other, and this synergy has been exploited in an enzyme immunoassay to detect HIV-I p24 in serum, plasma or other body fluids of HIV-I infected individuals.

In an especially preferred assay of the invention, monoclonal antibodies 31-42-19 and 31-90-25 are used together in solution as the probe to detect HIV-I p24, with polystyrene beads previously coated with anti-HIV-I human IgG as the capture antibodies. It has been found that 31-42-19 is the key monoclonal antibody which in combination with 31-90-25 results in optimal assay sensitivity for detection of HIV-I p24. Several alternate procedures can be employed to achieve the desired sensitivity and speed. In an alternate assay configuration, these two monoclonals can be successfully employed as capture antibodies for HIV-I p24 when coated on polystyrene beads.

Furthermore, monoclonal antibody 31-42-19 also recognizes HIV-2 p24. This unique characteristic of detecting both HIV-I p24 and HIV-2 p24 can be exploited in an immunoassay designed to screen non-discriminately for HIV infection. In addition, monoclonal antibody 31-42-19 can be used as a probe for the detection of HIV-2 p24.

Additionally, monoclonal antibody 31-90-25 can be employed as a competitive probe to detect anti-HIV-I core antibodies in biological samples.

DETAILED DESCRIPTION

The present invention provides a novel means for the detection of HIV-I p24 in picogram quantities in body fluids of infected individuals, using two monoclonal antibodies as a probe. This highly sensitive enzyme immunoassay is unique because of the characteristics of the monoclonal antibody 31-42-19. The epitope recognized by monoclonal antibody 31-42-19 maps toward the carboxy terminus of HIV-I p24 and is not immunogenic in humans. The second monoclonal antibody employed in this assay recognizes an epitope within a highly immunogenic region of HIV-I p24, and maps toward the amino terminus of HIV-I p24. Monoclonal antibodies 31-42-19 and 31-90-25 bind synergistically to HIV-I p24. Alternatively, one can employ F(ab')$_2$ or any antigen binding fragments of at least one of the monoclonal antibodies employed in the assay.

In addition, the epitope recognized by monoclonal antibody 31-42-19 is antigenically cross-reactive with an epitope on HIV-2 p24, as shown by the ability of 31-42-19 to immunoprecipitate HIV-2 p24 from biosynthetically labelled HIV-2 infected cells.

In addition to being employed as one of the components of the probe for HIV-I p24, the monoclonal antibody 31-90-25, when appropriately labelled, can be employed as a competitive probe against HIV-I core antibodies in serum samples for binding to recombinant-derived HIV-I p24. For example, HRPO labelled 31-90-25 can be employed in an immunoassay for antibodies to HIV as disclosed in U.S. patent application Ser. No. 020,282, filed Feb. 27, 1987 by Dawson et al., and commonly assigned herewith.

In another of its aspects, the present invention provides novel hybridoma cell lines, exemplified by murine-derived cell line ATCC HB 9726 and murine-derived cell line ATCC HB 9725, and novel monoclonal antibodies secreted thereby, exemplified by the above-noted monoclonal antibodies 31-42-19 and 31-90-25, repectively. The hybridoma cell lines producing monoclonal antibody 31-42-19 and monoclonal antibody 31-90-25 are deposited at the American Type Culture Collection, 12301 Parklawn Drive, Rockvill, Md. 20852 under deposit numbers ATCC HB 9726 for hybridoma 31-42-19 and ATCC HB 9725 for hybridoma 31-90-25, as of May 26, 1988.

In an especially preferred embodiment of the invention, a biological sample, presumably containing HIV-I p24, is incubated with a mixture of monoclonal antibodies 31-42-19 and 31-90-25, and a polystyrene bead coated with anti-HIV-I IgG (purified from serum of seropositive individuals for HIV-I p24 antibodies). After washing, the amount of mouse monoclonal antibodies bound, which is proportional to the amount of HIV-I p24 captured on the bead, is determined with horseradish peroxidase-labelled goat anti-mouse IgG. Alternatively, the monoclonal antibody mixture can also be coated on a solid phase to serve as capture antibodies. For example, this mixture can be used to coat a solid support of an immunoassay to detect HIV-I (HTLV-III) antigens as disclosed in U.S. Pat. No. 4,748,110, issued May 31, 1988.

In addition, the above-mentioned antibodies 31-42-19 and 31-90-25 can be employed in detection systems using fixed cells, with appropriate labelling of each monoclonal antibody. These antibodies also can be employed for purifying HIV-I p24, and the particular monoclonal 31-42-19 for purifying HIV-2 p24, by affinity chromatography.

Biological samples which are easily tested by the method of the present invention include human and animal body fluids such as whole blood, serum, plasma, cerebrospinal fluid and lymphocyte or cell culture supernatants. Additionally, the test samples could be inactivated whole virus or partially purified native or recombinant HIV-I p24. Solid supports which can be used in immunoassays of the invention include wells of reaction trays, test tubes, polystyrene beads, strips, membranes, microparticles, and other solid matrices known to those skilled in the art. Any label capable of producing a detectable signal or an enzyme amplification system can be used in immunoassays of the invention. Representative labels include enzymatic, radioisotopic, fluorescent and chemiluminescent labels. Further, hapten/labelled anti-hapten systems such as a biotin/-labelled anti-biotin system may be utilized in the inventive assays. Additionally, one can employ a labelled anti-idiotype antibody to detect the monoclonal antibodies described herein.

In addition, reagents for the assays of the invention are ideally suited for preparation of a kit. Such a kit may comprise carrier means being compartmentalized to receive in close confinement, one or more container means such as vials, bottles, test tubes and the like. Each of the container means comprises one of the separate elements to be used in the method of this invention.

The following illustrative examples serve to demonstrate the advantages of the invention, and relate (a) to the development and characterization of monoclonal antibodies which specifically react with certain epitopes of the HIV-I p24 core protein, and (b) to the development of a highly sensitive diagnostic test to detect HIV-I p24 in biological fluids. More specifically, Examples 1 and 2 relate to the procedures whereby hybridoma cell lines secreting monoclonal antibodies were generated. Example 3 relates to the screening, cloning and characterization of monoclonal antibodies 31-42-19 and 31-90-25. Example 4 relates to the method used for amplifying antibody yields. Example 5 relates to assays performed to determine the activity, specificity and epitope mapping of the 31-42-19 and 31-90-25 monoclonal antibodies. Example 6 relates to the development of an enzyme immunoassay (EIA) for the detection of HIV-I p24 in biological fluids using the above-mentioned monoclonal antibodies. Example 7 is a summary of alternate assay procedures covering the clinical utility of these monoclonal antibodies for AIDS diagnostics.

EXAMPLE 1

Immunization of Mice

In the procedure for production of hybridoma cell lines 31-42-19 and 31-90-25, BZH mice (obtained from Chella David, Department of Immunology, Mayo Clinic, Rochester, Minn.) were initially immunized with partially purified, detergent disrupted HIV-I (HTLV-III prototype strain obtained from R. C. Gallo, National Institute of Health) and boosted with recombinant derived purified p24 just before fusion. HIV-I was partially purified from infected H9 cells by (a) membrane filtration separating HIV-I from cells, followed by (b) concentration of cell culture fluid containing HIV-I, followed by (c) collection of virus by ultracentrifugation, followed by (d) resuspension of the virus and collection by centrifugation onto a 20% sucrose pad followed by (e) sucrose density gradient banding of HIV-I at a density of approximately 1.16 and (f) ultracentrifugation of banded virus to collect and concentrate HIV-I. HIV-I was disrupted by addition of 0.5% Triton X-100, followed by vigorous sonication at 4° C. Full-length recombinant HIV-I p24 was produced in *E. coli* by recombinant DNA methods and purified by affinity chromatography as disclosed in U.S. patent application Ser. No. 020,282. Briefly, a plasmid designated pB1, containing a 951 bp PvuII to Bg/II restriction fragment, was induced to produce full-length HIV-I p24, and then the recombinant HIV-I p24 was purified.

On day 1, mice received 10 μg disrupted HIV-I in 0.4 ml of Freund's Complete Adjuvant (Difco Laboratories) given subcutaneously (s.c.) and intraperitoneally (i.p.) in 0.1 ml portions at four different sites. The second immunization was performed 14 days later when mice received 10 μg of HIV-I in 0.3 ml of Freund's Incomplete Adjuvant, given s.c. and i.p. On day 29, mice were immunized with 10 μg HIV-I and 4 μg of S. typhimurium extract (RIBI Immunochemicals) in 0.2 ml Freund's Complete Adjuvant. On day 63, mice were immunized with 10 μg HIV-I in 0.2 ml Freund's Complete Adjuvant. Mice were bled on days 15, 36 and 70. The immune responses of the immunized mice were assessed by assaying their sera for anti-HIV-I antibody by enzyme-linked immunoassay and Western Blot. Approximately 14 months later, mice were immunized with a pre-fusion boost of recombinant HIV-I p24 antigen.

A. Enzyme-linked Immunoassay (EIA)

Sera from naive or immunized mice were serially diluted in dilution buffer containing 20 mM potassium phosphate, pH 7.4, 0.15M NaCl, 20% normal goat serum, 10% fetal calf serum, 5 mM EDTA, 10 mM EGTA, 50 mM Tris buffer (pH 8.0), 0.2% Tween-20, and sodium azide as preservative. The diluted sera were reacted with ¼" polystyrene beads directly coated with partially purified HIV-I, or, alternatively, with HIV-I bound to the bead via human anti-HIV-I antibody (purified from serum of an HIV-I seropositive individual). After 2 hours at 40° C., the beads were washed, and goat anti-mouse IgG (H+L) Horseradish Peroxidase (HRPO)-conjugated antibody (Kirkegaard & Perry Laboratories) was added. The beads were incubated at 40° C. for 2 hr, washed and transferred to reaction tubes containing o-phenylenediamine:2HCl (OPD) color reagent. The reaction was carried out in the dark at room temperature for 30 minutes, and then stopped by the addition of 1 ml of 1N $H_2SO_4$ and the absorbance at 492/600 nm was recorded. The absorbance was directly proportional to the amount of HIV-I specific mouse antibody bound to the bead. The specificity of mouse antibody for HIV-I antigen on the bead was confirmed by the addition of human HIV-I seropositive serum (20–50 μl) in the reaction as a competitor for binding to HIV-I antigens on the bead.

B. Western Blot

Approximately 500 μg of partially purified HIV-I were treated with sodium dodecyl sulfate (SDS) and 2-mercaptoethanol at 95° C., and electrophoresed in a 12% polyacrylamide-SDS gel (Laemmli et al., *Nature* (1970) 227:680–685). Proteins were transferred overnight from the gel to nitrocellulose by electrophoresis at 100 mamp, or transferred in 1–2 hr at 1.0 amp, in standard transfer buffer composed of 25 mM Tris (Hydroxymethyl Aminomethane), 192 mM glycine, and 2.0% methanol, pH 8.3. (Towbin et al., *Proc. Natl. Acad. Sci.* (1979) 73:4350–4354). After transferring the viral proteins and blocking the nitrocellulose with 20% fetal calf serum diluted in 10 mM Tris buffer (pH 8.0) containing 0.15M NaCl, the nitrocellulose was cut into strips (each strip containing approximately 15 μg of viral protein) which were then used to determine the presence of anti-HIV-I antibody in test sera (or other samples). Reaction mixtures consisted of a nitrocellulose strip incubated with an appropriate amount of test sample in 2.5 ml of buffer (20 mM Tris, 1 mM EDTA, 0.2M NaCl, 0.3% Triton X-100, and 2 mg/ml bovine serum albumin, pH 7.5) for 1–2 hours at room temperature. The strips were washed with buffered detergent (10 mM phosphate buffered saline (PBS), pH 7.5, containing 0.1% SDS and 0.5% Triton X-100), followed by addition of goat anti-mouse IgG antibody conjugated to HRPO. The strips were incubated for 1–2 hours at room temperature, followed by washing with buffered detergent. Finally, antibody bound to viral protein was visualized by addition of freshly prepared HRP color reagent (Biorad) (120 mg dissolved in 40 ml ice-cold methanol, then diluted into 200 ml Tris buffered saline, pH 7.8, containing 120 μl of 30% hydrogen peroxide). This assay demonstrated the presence of antibody to specific HIV-I proteins.

EXAMPLE 2

Cell Fusion

Upon demonstration of specific anti-HIV-I antibody present at reasonable titers in sera of immunized mice, the mice were allowed to rest prior to a pre-fusion boost of antigen. The pre-fusion antigen boost was performed by intravenous (tail vein) injection of approximately 200 μl of purified recombinant HIV-I p24. Three days later the mice were sacrificed, and their spleens, containing anti-HIV-I antibody producing cells, were disrupted to single cells. The single cell suspensions were treated with 0.83% $NH_4Cl$ to remove red blood cells, and then mixed with SP2/0 cells at a 10:1 (SP2/0:spleen cells) ratio. The mixed cells were centrifuged, washed once with serum-free medium, then centrifuged again. The fusogen, polyethylene glycol (PEG), was used to form hybrids of the immune donor spleen cells with the myeloma cell line SP2/0 (HPRT neg.) [Kohler and Milstein, *Nature* (1975) 256:494, and reviewed in *Monoclonal Hybridoma Antibodies: Techniques and Applications*, ed. Hurrell (CRC Press, Inc., 1982)]. Briefly, fusion of the spleen and SP2/0 cells was accomplished by exposing the pellet to 40% PEG (ATTC, MW 1300–1600) in serum-free Iscoe's Modified Dulbecco's Medium (IMDM) for two minutes. The PEG and cell suspension was diluted slowly by the addition of 20 ml of serum-free IMDM over a period of five minutes, followed by colleciton of the cells by centrifugation. The supernatant was decanted and replaced with 30 ml IMDM containing 20% fetal bovine serum (Hyclone) with HAT (hypozanthine, aminopterin, and thymidine) to select for hybridomas. Spleen cells from one nonimmune Balb/c mouse also were added as a feeder layer. The cells were plated at 0.1 ml/well in three 96 well tissue culture plates. Three days later an additional 0.1 ml of HAT media was added to each well. At weekly intervals thereafter, one-half the media was replaced with IMDM containing 20% fetal bovine serum (Hyclone) with HT (hypozanthine and thymidine), and hybrids were allowed to grow for an additional 7-14 days.

Some of the hybrids were composed of spleen cells making antibody to HIV-I fused with SP2/0 cells. Briefly, the fusogen promotes fusion of spleen cell and SP2/0 cell membranes, forming a heterokaryon containing nuclei of both cells. Eventually, the dissimilar nuclei fuse producing a single nucleus capable of synchronous mitosis. As the fused cells divide, the hybrid stabilizes by losing chromosomes of each nucleus. The fused cells are plated into multiple 96 well plates at $10^5$ to $10^6$ cells per well. Hybrid cells formed from SP2/0:spleen cell fusions are selectively propagated by culturing in HAT medium. All unfused SP2/0 or SP2/0:SP2/0 fused cells are prevented from growing by aminopterin, and unfused spleen cells or spleen:-spleen fused cells die off in culture. Only SP2/0:spleen hybrids will grow in the HAT selection medium.

EXAMPLE 3

Screening, Cloning and Characterization of Monoclonal Antibodies 31-42-19 and 31-90-25

After 10-14 days, culture fluids from wells containing hybridoma cell growth were screened for antibody to HIV-I p24 using EIA and Western Blot procedures described in Example 1. In addition, an EIA using HIV-I p24 produced in *E. coli* by recombinant DNA methods (rp24) was employed for screening. Briefly, polystyrene beads coated with human IgG (purified from anti-p24 seropositive individuals) were reacted with crude *E. coli* extracts of full-length recombinant-derived HIV-I p24. The resultant beads, bearing rp24 bound via human anti HIV-I antibody, were reacted with hybridoma culture fluids for 4 hr at 40° C. or overnight at room temperature, washed and reacted with HRPO-labelled goat anti-mouse IgG (Fc) for 2 hr at 40° C. After washing again, beads were transferred to reaction tubes for the addition of OPD substrate as described in Example 1.

From a single fusion, #31, twenty-one wells were identified as showing hybridoma cell growth and colony formation. Culture fluid from each well was screened for antibody to HIV-I p24 by EIA and Western Blot. Of 21 wells, 15 were identified as hybrids containing antibody to HIV-I p24. Cells from each of these 15 wells were expanded in multiple 24 well plates, and culture fluid was again assayed for the presence of anti-HIV-I p24 antibody, and confirmed by competition EIA with human anti-HIV-I serum as described in Example 1. All 15 were positive for anti-HIV-I p24 antibody and each hybrid was further expanded in T25 flasks for cloning by limiting dilution. Each expanded hybrid was plated into 96 well microtiter plates at dilutions of $10^5$ to $10^6$ and allowed to grow from 10-21 days. Among thirteen hybrids having clones identified as producing antibodies to HIV-I p24 were clones #19 from hybrid #42 of fusion #31, named accordingly 31-42-19, and #25 from hybrid #90 of fusion #31, named accordingly 31-90-25. The clones were obtained by limiting dilution using the guidelines outlined by J. W. Goding in *Monoclonal Antibodies: Principles and Practice* (Academic Press, N.Y., 1983).

The isotype of monoclonal antibody 31-42-19 was determined to be IgG1 and that of monoclonal antibody 31-90-25 was determined to be IgG2a. An EIA isotyping procedure employed a microtiter plate coated with goat anti-mouse immunoglobulin, which was incubated with culture fluid of the clone to capture the secreted mouse antibody. After 2 hours, the plate was washed and rabbit anti-mouse isotype was applied for an additional 2 hours. The plate was washed again, and HRPO-conjugated goat anti-rabbit IgG was applied for 1 hr. The excess conjugate was removed by washing, then OPD substrate was added. The amount of rabbit anti-mouse isotype bound to mouse immunoglobulin was proportional to the absorbance measured at 492 nm. Further characterization of both monoclonals was performed with antibodies from mouse ascites.

EXAMPLE 4

Amplification of antibody yields by ascites method

In order to obtain greater amounts of monoclonal antibodies, ten to 20 million cloned cells of the desired antibody (31-42-19 or 31-90-25) were inoculated into a Balb/c mouse previously treated intraperitoneally with 0.5 ml pristane (2,6,10,14-tetramethylpentadecane) [method outlined in Hurrell et al., supra]. Pristane treatment enhances growth of mouse myeloma hybrids within the peritoneum of the mouse, and the ascites fluids which form are rich in the monoclonal antibody secreted by the hybrid cells. After formation of monoclonal antibody enriched ascites (approximately 7 days) the mice were sacrificed and the ascites was withdrawn from the peritoneum, clarified by centrifugation and stored at −20° C. Other characterization procedures (described herein) were performed with culture fluid, clarified ascites or purified antibodies from ascites, using protein A sepharose (Hurrell et al., supra). The monoclonal antibody in ascites was titered by EIA (Example 5).

EXAMPLE 5

Activity, Specificity and Epitope Mapping

The following experiments were carried out for both monoclonal antibodies 31-42-19 and 31-90-25 to assess their activity, specificity and epitope recognition profile.

A. EIA

Assays described in Examples 1 and 3 were used to determine the titer of monoclonal antibodies. Briefly, clarified ascites fluids or protein A-purified IgG were reacted in serial dilutions against polystyrene beads coated with recombinant-derived HIV-I p24 bound to beads via human IgG (purified from sera of HIV-I seropositive individuals). Representative data, as illustrated in Table 1, shows the specific reactivity of the monoclonal antibodies when compared to the negative control. In addition, two assays were performed in which purified IgG from an established HIV-I seropositive individual was used as a competitive inhibitor to determine the human immunogenicity of the epitopes recognized by 31-42-19 and 31-90-25. In one procedure, human anti-HIV-I IgG was serially diluted in dilution buffer (described in Example 1) containing a constant amount of either 31-42-19 or 31-90-25. In the other procedure, human anti-HIV-I IgG was added at a constant concentration (1 μg/ml) to serial dilutions of each of the monoclonals. The human IgG served as a competitive inhibitor for the binding of mouse monoclonal antibody to HIV-I rp24 on beads. Competition of anti- HIV-I IgG with each monoclonal was indicated by a reduction in the amount of monoclonal antibody bound to the bead when compared to the control which contained no competing human IgG. Representative data, as illustrated in Tables 2 and 3, shows that 31-42-19 recognizes an epitope not readily immunogenic in humans, while 31-90-25 recognizes an epitope within a highly immunogenic region of HIV-I p24. Table 3 data shows, however, that gross excesses of human anti-HIV-I IgG can block the binding of 31-42-19 to some extent.

TABLE 1

Activity of Monoclonal Antibodies 31-42-19 and 31-90-25 Against HIV-I rp24.

| Antibody Concentration(μg/ml) | Absorbance (492 nm) | |
|---|---|---|
| | 31-42-19 | 31-90-25 |
| 1.0 | 1.436 | 1.767 |
| 0.5 | 1.305 | 1.771 |
| 0.25 | 1.250 | 1.717 |
| 0.125 | 1.215 | 1.731 |
| 0.0625 | 1.063 | 1.772 |
| 0.0312 | 0.848 | 1.719 |
| 0.0156 | 0.708 | 1.415 |
| 0.0078 | 0.484 | 1.131 |
| Neg. Control[a] | 0.028 | 0.044 |

[a]Negative control contained only dilution buffer and served as reagent blank.

TABLE 2

Competition Profile with Serial Dilution of Human Anti-HIV-I IgG.

| Human IgG | Absorbance (492 nm) | |
|---|---|---|
| | 31-42-19[a] | 31-90-25[b] |
| Undiluted | 2.300 | 0.116 |
| Dilution #1 | 2.320 | 0.181 |
| Dilution #2 | 2.216 | 0.181 |
| Dilution #3 | 2.500 | 0.264 |
| Dilution #4 | 2.134 | 0.377 |
| Dilution #5 | 2.043 | 0.595 |
| Dilution #6 | 2.305 | 0.822 |
| Dilution #7 | 2.301 | 1.064 |
| Dilution #8 | 2.165 | 1.467 |
| Control | 2.282 | 1.401 |

[a]31-42-19 added at 0.1 μg/ml, anti-HIV-I human IgG added at 1.0 μg/ml in the first well and serially diluted in the next eight wells.
[b]31-90-25 added at 2.0 μg/ml, anti-HIV-I human IgG added at 20 μg/ml in the first well and serially diluted in the next eight wells.

TABLE 3

Competition Profile with Serial Dilution of 31-42-19 and 31-90-25.

| Antibody Concentration(μg/ml) | Absorbance (492 nm) | | | |
|---|---|---|---|---|
| | 31-42-19 | | 31-90-25 | |
| | control | +anti-HIV-I | control | +anti-HIV-I |
| 1.0 | 1.436 | 1.412 | 1.767 | 0.612 |
| 0.5 | 1.305 | 1.315 | 1.771 | 0.461 |
| 0.25 | 1.250 | 1.223 | 1.717 | 0.383 |
| 0.125 | 1.215 | 1.069 | 1.731 | 0.255 |
| 0.0625 | 1.063 | 1.034 | 1.772 | 0.152 |
| 0.0312 | 0.848 | 0.663 | 1.799 | 0.108 |
| 0.0156 | 0.708 | 0.448 | 1.415 | 0.056 |
| 0.0078 | 0.484 | 0.353 | 1.131 | 0.053 |

B. Radioimmunoprecipitation assay

The specificity of monoclonal antibodies 31-42-19 and 31-90-25 was confirmed by immunoprecipitation of [35S] methionine/[35S] cysteine biosynthetically-labelled viral p55 (gag precursor protein) from HIV-I infected H9 cell lysates. Immunoprecipitation assays for viral proteins have been described previously (Devare et al., *Proc. Natl. Acad. Sci.*, U.S.A. (1986) 83: 5718-5722). Cell lines employed for these studies were uninfected H9 cells, HIV-I infected H9 cells or a cloned cell line S5G7 derived from infected H9 cells, which produces large quantities of virus. Cells were harvested from culture, washed once with RPMI 1640 deficient in methionine and cysteine (Gibco Laboratories), then suspended at 1-2.5 X 10$^6$ cells/ml in the same medium. Washed cells were incubated for 30-45 minutes at 37° C. in 6% CO$_2$, followed by the addition of 50-100 μCi each of [35S] methionine and [35S] cysteine (Amersham) to the medium. Cells were radiolabelled at 37° C. for 4-8 hours, harvested by centrifugation and lysed in PBS, pH 7.4, containing 1 mM PMSF, aprotinin (100 kallikrein inactivation units per ml of buffer), 1.0% Triton X-100, 0.1% SDS and 0.5% sodium deoxycholate (all reagents from Sigma). The lysate was clarified by centrifugation at 100,000×g for 40 minutes and stored at −70° C.

Figure 1:
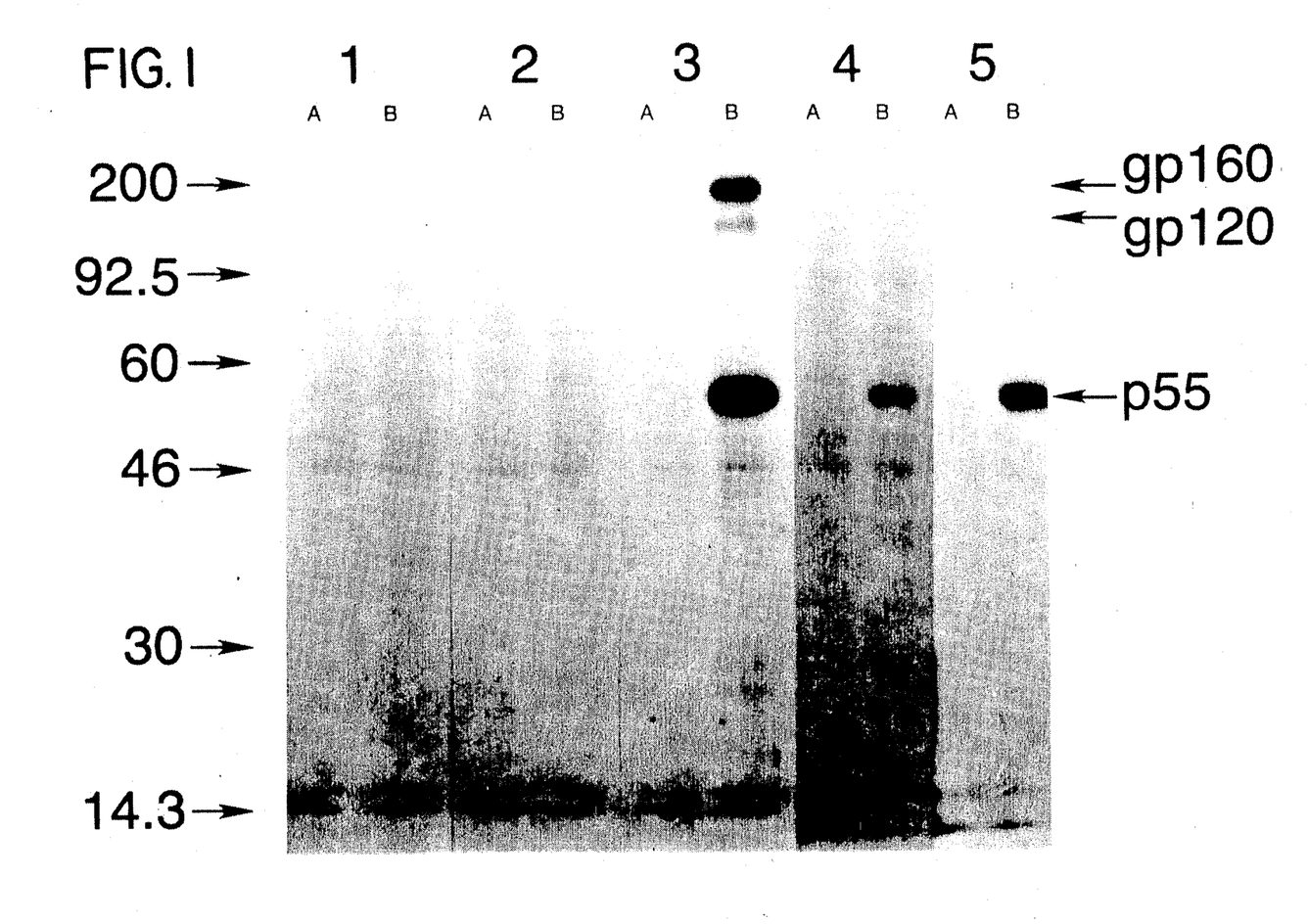
FIG. 1 is an autoradiograph showing the specificity of monoclonal antibodies 31-42-19 and 31-90-25 for HIV-I p24 by immunoprecipitation of metabolically radiolabelled HIV-I p55.

Immunoprecipitation was performed by incubating 100 μl aliquots of cell lysates with 50 μg purified monoclonal antibody (1.0 mg/ml stock), 100 μl tissue culture supernatant or 3 μl serum for 30-60 minutes at 4° C. Antigen-antibody complexes were recovered by addition of 200 μl of preswollen protein A-Sepharose (Pharmacia) previously washed in lysis buffer containing 1.0 mg/ml bovine serum albumin (IgG binding capacity of 50-200 μg/200 μl protein A). The reaction mixture was shaken vigorously at 4° C. for 1 hour, followed by 3 washes of Protein A-Sepharose using lysis buffer. Protein A-Sepharose was then collected by centrifugation and immune complexes were dissociated by heating at 95° C. in SDS gel sample buffer containing 2-mercaptoethanol (Laemmli et al., supra). The sample was subjected to SDS-10% polyacrylamide gel electrophoresis. The gel was incubated for 30 minutes in Enhance (Dupont), dried and exposed to X-ray film for autoradiography of the immunoprecipitated radiolabelled proteins. The results are illustrated in FIG. 1 where, in Panel A, labelled cell lysates from uninfected H9 cells, and, in Panel B, lysates from HIV-I infected H9 cells (S5G7 cell line) were mixed with (1) normal mouse serum, (2) normal human serum, (3) HIV-I immune human serum, (4) monoclonal antibody 31-42-19 tissue culture supernatant and (5) monoclonal antibody 31-90-25 tissue culture supernatant. The results indicated that both monoclonal antibodies immunoprecipitated gag precursor p55 from HIV-I infected cells. No detectable cross reactivity was observed with any other radiolabelled viral or cellular protein. Thus, both monoclonal antibodies bound specifically to HIV-I p55.

Figure 2:
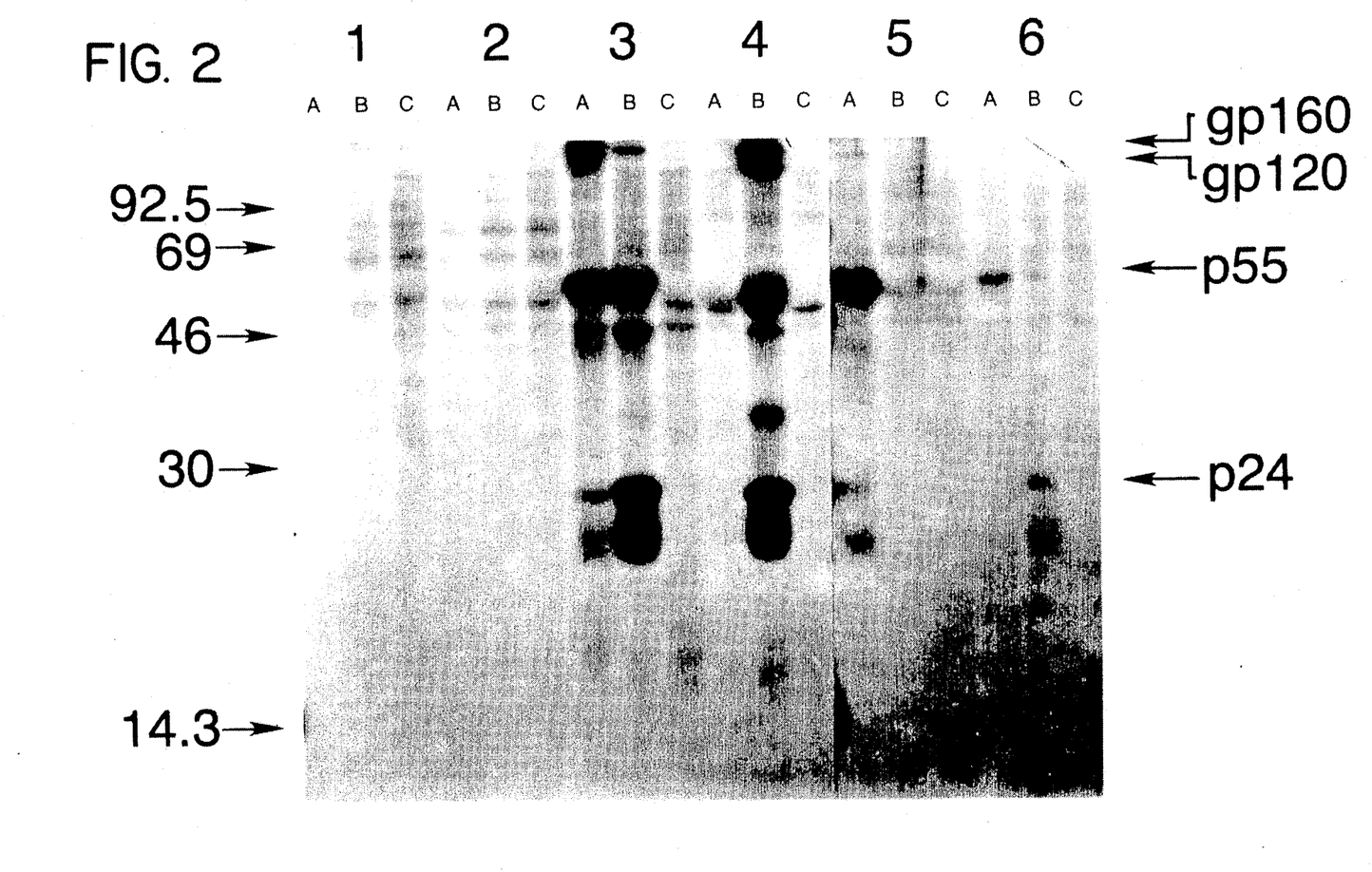
FIG. 2 is an autoradiograph showing reactivity of 31-42-19 and 31-90-25 with HIV-I and HIV-2 as labelled antigen; more specifically, showing cross reactivity of 31-42-19 with HIV-2 p24.

In addition, each monoclonal antibody also was reacted with labelled cell lysates of HIV-I infected HUT 78 cell line (Panel A), HIV-2 infected HUT 78 cell lines (Panel B), and uninfected HUT-78 cell lines (Panel C). Results are illustrated in FIG. 2, wherein each of these cell lysates was reacted with (1) normal mouse serum, (2) normal human serum, (3) serum from an HIV-I seropositive individual, (4) serum from an HIV-2 seropositive individual, (5) monoclonal antibody 31-90-25 and (6) monoclonal antibody 31-42-19. Results indicated that monoclonal antibody 31-42-19 specifically immunoprecipitates HIV-2 p24. No cross reactivity with HIV-2 p24 was observed with monoclonal antibody 31-90-25, or with normal mouse serum, which indicates that it is a unique characteristic of monoclonal antibody 31-42-19 that allows it to cross react with an epitope on HIV-2 p24.

C. Western Blot Analysis

Figure 3:
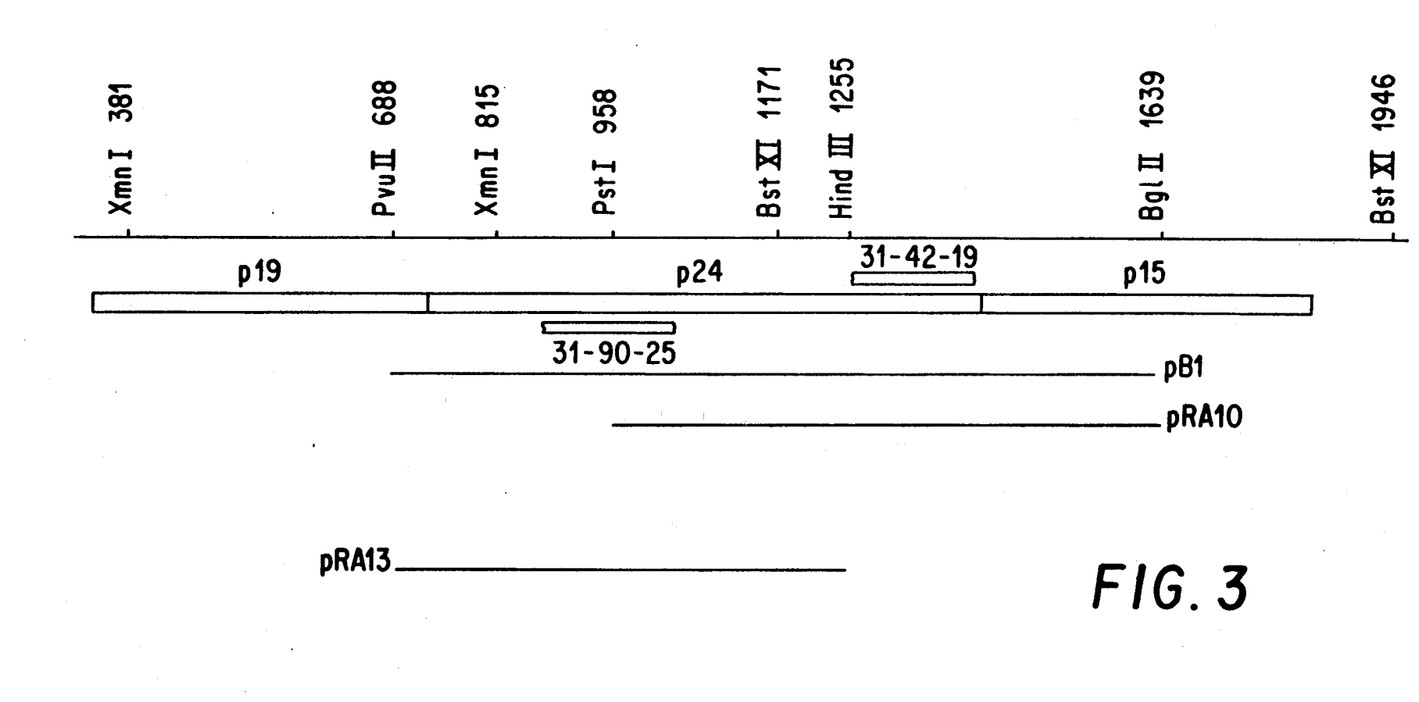
FIG. 3 is a schematic representation of the recombinant deletion clones used for epitope mapping and approximate location of epitopes recognized by monoclonal antibody 31-42-19 and 31-90-25.
Figure 4:
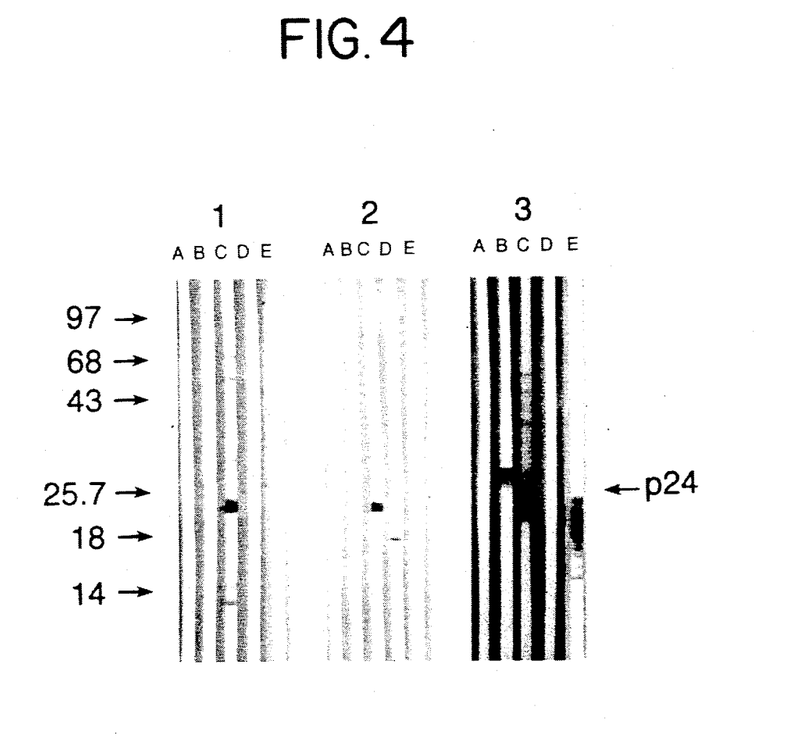
FIG. 4 is a Western Blot showing specificity of monoclonal antibodies 31-42-19 and 31-90-25 for HIV-I p24 and their epitope recognition profiles.

Western blots (as described in Example 1) of purified monoclonal antibodies 31-42-19 and 31-90-25 were performed using partially purified HIV-I virus, and, recombinant full-length p24 and p24 deletion clones as antigens to further establish specificity and for epitope mapping, respectively. Partially purified HIV-I or crude cell extract of *E. coli*-derived recombinant HIV-I p24 clones (see FIG. 3 which shows a schematic representation of clones used) was electrophoretically transferred to each nitrocellulose strip after electrophoresis in a 12% polyacrylamide gel under reducing conditions. As shown in FIG. 4, Panel A was a control of *E. coli* (untransformed) cell lysates; Panel B used full-length recombinant clone pB1 as antigen; Panel C, HIV-I viral lysate; Panel D, recombinant deletion clone pRA10 and Panel E, recombinant deletion clone pRA13. The results confirmed that both monoclonal antibodies specifically react with HIV-I p24 when tested against lysates of partially purified virus. Further, the reaction of each monoclonal antibody with recombinant deletion clones of HIV-I p24 indicated that 31-42-19 maps toward the carboxy half of HIV-I p24 while 31-90-25 maps toward the amino terminus of HIV-I p24. These results also were confirmed by comparing serological data and competitive RIA (radioimmunoassays) with other members of HIV-I p24 monoclonal panel (data not shown here).

D. Immunocytochemical Assay (ICA)

Monoclonal antibodies 31-42-19 and 31-90-25 were employed in an immunocytochemical assay against uninfected and HIV-I infected H9 cells in order to further demonstrate their specificity for HIV-I. Briefly, uninfected or HIV-I infected H9 cells were fixed to microscope slides using 100% acetone for 10 min., then air dried, and stored at −20° C. For staining, the cells were rehydrated in PBS for 10 min., followed by addition of 100 μl of 2% normal goat serum in PBS containing 100 μg/ml normal human IgG for 10 min. Excess reagent was removed, and 100 μl of 1 μg/ml 31-42-19 IgG or 31-90-25 IgG were added for 30 min. to the slides maintained in a humidified chamber. The slides were washed in PBS, followed by addition of 100 μl of a second antibody, goat anti-mouse IgG (Pel Freez) at a 1:400 dilution, for 30 min. The slides were washed with PBS, followed by addition of 100 μl of peroxidase antiperoxidase complex (Clonal PAP, Sternberger and Meyer) diluted 1:300 in PBS containing 2% normal goat serum and 100 μg/ml normal human IgG. The slides were incubated (with the Clonal PAP) in a humidified chamber. After washing in PBS, color development was initiated by the addition of 100 μl of the chromagen (0.63 mg/ml tetra hydrochloride diamino-benzidine in 0.06% hydrogen peroxide in PBS). Color development was stopped after 6 min. by washing the slides in tap water. The slides were dehydrated and mounted for examination.

Results indicated that the monoclonal antibodies did not cross react with any normal cellular constituents. Specific staining was only detected with HIV-I infected H9 cells which was characteristic of HIV-I anti-p24 monoclonals.

EXAMPLE 6

Enzyme-linked Immunoassay (EIA) for the Detection of HIV-I p24 in Biological Fluids A. Selection of Monoclonal Combination A panel of anti-HIV-I p24 monoclonal antibodies was tested in a three step assay configuration. Briefly, 200 μl HIV-I antigen sample (1.0 ng/ml partially purified HIV-I viral lysate, diluted in normal human plasma [NHP]) was incubated with a ¼" polystyrene bead coated previously with anti-HIV-I human IgG overnight at room temperature. After washing, 200 μl of either a single monoclonal antibody solution or a monoclonal antibody mixture solution (each monoclonal in equal proportion), at a final concentration of 5 μg/ml diluted in NHP, was added. The reaction mixture was incubated at 40° C. for 4 hr. After washing, the amount of each monoclonal bound to the bead was detected using HRPO labelled goat anti-mouse IgG. The detection steps were carried out as described in Example 1. Absorbance at 492 nm was directly proportional to the amount of mouse monoclonal antibodies bound to the HIV-I p24 captured on the bead. Data in Tables 4 and 5 demonstrate that 31-42-19 drives the synergistic binding with 31-90-25 because any monoclonal mapping in the region of 31-90-25 bound synergistically to HIV-I p24 in the presence of 31-42-19. Monoclonal antibodies 31-7-20, 31-32-9, 31-77-8, 31-89-8, 32-51-16 and 31-90-25 all recognize the same epitope on HIV-I p24. Therefore, 31-42-19 is the key monoclonal antibody which binds synergistically with 31-90-25, resulting in optimal binding between human anti-HIV-I IgG on the bead, HIV-I p24 and the monoclonals.

TABLE 4

Synergy Between Monoclonal Antibodies to HIV-I p24 Tested as Probes for HIV-I p24 Antigen Assay.

| Probe | Net O.D. (492 nm) |
|---|---|
| 31-42-19 alone | 0.498 |
| 31-90-25 alone | 0.468 |
| 32-51-16 alone[a] | 0.494 |
| 31-74-22 alone[b] | 0.095 |
| 31-79-18 alone[c] | 0.034 |
| 31-42-19 + 31-90-25 | 1.211 |
| 31-42-19 + 32-51-16 | 1.189 |
| 32-51-16 + 31-90-25 | 0.484 |
| 31-42-19 + 31-90-25 + 32-51-16 | 1.241 |

[a]Monoclonal antibody 32-51-16 recognized the same epitope as 31-90-25 but was generated from a different fusion experiment.
[b]Monoclonal antibody 31-74-22 recognized an epitope near the amino terminus of HIV-I p24, but different from the epitope of 31-90-25.
[c]Monoclonal antibody 31-79-18 recognized an epitope near the carboxy terminus of HIV-I p24.

TABLE 5

Synergistic Characteristics of 31-42-19 and Epitope Specificity of Synergy Between 31-42-19 and a Group of Monoclonals to HIV-I p24.

| Monoclonal Mixture | Absorbance (492 nm) |
|---|---|
| 31-42-19 + 31-7-20 | 1.219 |
| 31-42-19 + 31-32-9 | 1.156 |
| 31-42-19 + 31-77-8 | 1.128 |
| 31-42-19 + 31-89-8 | 1.354 |
| 31-42-19 + 32-51-16 | 1.190 |
| 31-42-19 + 31-90-25 | 1.355 |
| 31-42-19 + 31-79-18 | 0.658 |
| 31-90-25 + 31-77-8 | 0.452 |

During further investigations, the monoclonals were employed in the development of a two step (overnight/2 hr) assay for the detection of HIV-I p24 (detailed herein). A sensitivity panel of p24 enriched antigen was prepared with partially purified HIV-I viral lysate diluted in NHP in the concentration range from 500 to 31.25 pg protein/ml. Each panel member was assayed using each of the below-listed monoclonal antibody mixtures as a probe. An absorbance value which was 0.05 O.D. units greater than that of the negative control was considered the cut-off value for the assay, and samples showing higher absorbance values than the cut-off were considered positive. The sensitivity, defined as picograms of HIV-I p24 per ml that gave an absorbance value of 0.05 O.D. units greater than that of the negative control, was determined by linear regression. Monoclonal antibody 31-90-25 was selected from a group of monoclonals mapping to the same general region of HIV-I p24 because it produced the most sensitive results in the two step assay configuration, as demonstrated in Table 6.

TABLE 6

Comparison of the Sensitivity of Two Step HIV-I p24 Antigen Assay, replacing 31-90-25 with Other Monoclonals which Map to Same Epitope.

| Monoclonal Mixture | Sensitivity in pg/ml antigen |
| --- | --- |
| 31-42-19 + 31-90-25 | 23.9 |
| 31-42-19 + 31-7-20 | 126.0 |
| 31-42-19 + 31-32-9 | 73.0 |
| 31-42-19 + 31-77-8 | 97.0 |
| 31-42-19 + 32-51-16 | 62.0 |

B. Assay Configurations for HIV-I p24 detection

Experimental data detailed herein describe the preferred assay configurations for the detection of HIV-I p24 in biological fluids. Experimental conditions of incubation time and temperature can be varied according to the requirements of speed of the assay and sensitivity.

Monoclonal antibodies 31-42-19 and 31-90-25 used in the assay were purified from either tissue culture supernatants or mouse ascites fluids using protein A-Sepharose. Protein determinations of purified IgG was done by measuring absorbance at 280 nm.

1. Monoclonals in Solution Used as a Probe

A mixture of monoclonal antibodies was prepared as a stock solution containing 25 $\mu$g IgG/ml with a 31-42-19 to 31-90-25 ratio of 4:6, in a diluent of 20 mM phosphate buffer, pH 7.4, 0.15M NaCl, 25% NHP (v/v), 1% bovine serum albumin (w/v) and 0.25% Triton X-100 (v/v). When 50 $\mu$l of this solution was added to 200 $\mu$l of assay sample, it gave a final concentration of monoclonal mix at 5 $\mu$g/ml in the assay volume. The ratio of both monoclonal antibodies and the IgG concentration were found to be satisfactory under the assay conditions used, although variations in the mixture can be made to meet lot to lot variations of the monoclonal antibody preparations.

For the assay procedure, briefly, 50 $\mu$l of monoclonal mix was added to reaction tray wells followed by 200 $\mu$l of either (a) a sample presumably containing HIV-I p24, (b) a sensitivity panel member with known amounts of either partially purified HIV-I virus or native p24 diluted in NHP as positive control or (c) plasma from an established uninfected individual as negative control. A $\frac{1}{4}$" polystyrene bead previously coated with anti-HIV-I human IgG was added to each reaction well. The reaction mixtures were incubated at room temperature overnight (12-18 hr). After washing beads with water, 200 $\mu$l of conjugate solution were added to each reaction well. The conjugate solution was prepared by diluting HRPO labelled goat anti-mouse (Y) IgG (Kirkegaard & Perry) or HRPO labelled goat anti-mouse (Fc) IgG (Jackson Immunochemicals) in a diluent containing 20 mM phosphate buffer, pH 7.4, 0.15M NaCl, 10% fetal calf serum (v/v), 15% normal goat serum (v/v), 25% NHP (v/v), 5% normal rabbit serum (v/v), 0.025% benzyl alcohol (v/v), 0.5% Triton X-100 (v/v) and 20 mM HEPES (N-2-Hydroxyethylpiperazine-N'-2-ethane sulphonic acid). The reaction mixtures were incubated at 40° C. for 2 hr in a waterbath. After washing, the beads were transferred to reaction tubes and the addition of OPD carried out as described in Example 1.

Additionally, shorter assay incubation times are possible by incubating the antigen sample, monoclonal mix and beads at 40° C. in a waterbath or in a dynamic incubator for 4-6 hr, and incubating the conjugate solution for 1 hr at 40° C. Table 7 shows that both Monoclonal assay procedures have improved sensitivity when compared to the current Polyclonal HIV-I antigen assay.

TABLE 7

| Assay Format | Sensitivity (pg p24/ml) | |
| --- | --- | --- |
| | HIV-I | HIV-I p24 |
| Abbott Polyclonal HIV-I Ag Assay (ON RT/4 hr 40° C./2 hr 40° C.) | 44.0 | 7.0 |
| Monoclonal Assay (ON RT/2 hr 40° C. or 1 hr 40° C.) | 21.5 | 3.0 |
| Monoclonal Assay (6 hr/1 hr 40° C.) | ND | 5.3 |

ON = Overnight; RT = Room Temperature; ND = Not Done

2. Alternate Assays

Alternatively, monoclonal antibodies 31-42-19 and 31-90-25 can be successfully coated on $\frac{1}{4}$" polystyrene beads for use as capture antibodies for HIV-I p24. Briefly, the monoclonal antibody mixture was coated at an appropriate concentration on polystyrene beads. Additional binding sites were overcoated with bovine serum albumin. In an assay procedure, the antigen sample containing HIV-I p24 was incubated with the coated beads. After appropriate incubation, beads were washed and HIV-I p24 bound was detected using a suitable probe. An especially preferred probe used comprised F(ab')$_2$ fragments prepared from purified anti-HIV-I rabbit IgG, as disclosed in an U.S. patent application, entitled "Immunoassay for HIV-I Antigens Using F(ab')$_2$ Fragments as Probe," filed by J. Stewart et al. concurrently with this application.

Monoclonal antibody 31-42-19 exhibited similar synergistic characteristics when either used as a probe in solution or as a capture antibody on the bead in combination with monoclonal antibody 31-90-25.

C. Detection of HIV-2

The assay described in section B.1 of this example was used to detect purified HIV-2 p24. Data indicated that the present assay configuration was able to detect 800 pg/ml HIV-2 p24 using anti-HIV-I human IgG as capture antibody on the bead. Increased sensitivity of the assay can be achieved by using HIV-2 specific capture antibodies. In addition, 31-42-19 monoclonal antibody used alone as a probe at 5 $\mu$g/ml assay concentration gave a sensitivity equivalent to that of the monoclonal mixture. These results were expected since 31-90-25 does not cross react with HIV-2 p24.

D. Clinical Utility of Monoclonal Based HIV-I Antigen Assay

The clinical utility of the monoclonal based HIV-I antigen assay was assessed by comparing it to the Abbott HIV-I antigen assay of established clinical efficacy (Paul et al., supra). Approximately 485 clinical samples from ARC, AIDS or high risk, asymptomatic patients were received from Rush Presbyterian St. Luke's Medical Center, Chicago, Ill., and tested over a period of 1 year. Each of the samples was tested with the Abbott HIV-I antigen assay and the ON RT/2 hr 40° C. Monoclonal assay. An absorbance value which was 0.05 O.D.

units greater than that of the negative control was considered the cut-off value for both assays, and samples showing higher absorbance values than the cut-off were considered positive. All positive samples were confirmed by the Abbott HIV-I neutralization assay procedure. Briefly, HIV-I antigen positive samples were incubated with an excess of serum or purified lgG from an established HIV-I seropositive individual with high HIV-I anti-p24 titers. After preincubation at room temperature, the residual (not neutralized) p24 was detected using either the Abbott HIV-I antigen assay or the Monoclonal assay. True HIV-I positive samples showed drastic reductions in O.D. units at 492 nm. Any sample that showed greater than 50% neutralization in the presence of anti-HIV-I antibodies compared to that of the control, which contained same amount of normal human lgG or plasma, was considered confirmed positive. Non-neutralizable positive samples were considered negative for HIV-I antigen. Data are summarized in Table 8.

TABLE 8

Comparative Profile of Clinical Samples.

| | Monoclonal HIV-I Ag Assay | |
|---|---|---|
| | Pos | Neg |
| Abbott HIV-I Ag Assay | | |
| Pos | 165 | 7[a] |
| Neg | 31[b] | 282 |

[a]Monoclonal assay missed 7 samples, of which 4 were serial bleeds from two patients.
[b]Abbott antigen assay missed 31 samples, of which 22 samples were serial bleeds-2 samples from patient A, 3 samples from patient B, 4 samples from patient C, 2 samples from patient D and 11 samples from patient E.

As shown in Table 8, the majority of samples are in good agreement with the Abbott HIV-I antigen assay. Those samples which were discrepant seemed to follow a pattern—(a) for the majority (4 of 7) of positive samples missed by the Monoclonal assay, their absorbance values were very close to the cut-off value of the Abbott HIV-I antigen assay, (b) the Monoclonal assay (with the neutralization assay) confirmed the samples missed by the Abbott HIV-I antigen assay (28 of 31, 3 samples could not be confirmed due to lack of sample volume) partly due to better sensitivity of the Monoclonal assay (see Table 7), (c) there seems to be a patient-specific pattern, i.e. all samples of that patient were missed, when either the Monoclonal assay or the Abbott HIV-I antigen assay missed a sample from a particular patient.

In addition, several established seroconversion panels were tested. These panels were also tested by several other commercially available or in-house tests for HIV-I antibodies and antigen. These comparisons show that the Monoclonal antigen assay is highly effective in detecting seroconversion in longitudinal studies. For example, as shown in Table 9, using an in-house seroconversion of panel, both the Abbott HIV-I antigen assay and the Monoclonal assay detected the seroconversion of an AIDS-infected individual at the same time point that antibodies to HIV-I env proteins were detected by an HIV-I antibody immunoassay, and before HIV-I core antibodies were detected. Similarly, in another seroconversion panel purchased from Boston Biomedica, the Monoclonal assay detected the presence of HIV-I antigen at the same time point antigen was also detected by the ENI antigen assay (ENI antigen assay results were supplied by Boston Biomedica).

TABLE 9

| | In-house Seroconversion Panel. | | | |
|---|---|---|---|---|
| | Anti-HIV-I Ab | | HIV-I Antigen | |
| Bleed No. | Core | Env | Abbott Ag | Monoclonal |
| 1 | − | − | − | − |
| 2 | − | − | − | − |
| 3 | − | − | − | − |
| 4 | − | − | − | − |
| 5 | − | − | − | − |
| 6 | − | − | − | − |
| 7 | − | − | − | − |
| 8 | − | − | − | − |
| 9 | − | − | − | − |
| 10 | − | − | − | − |
| 11 | − | + | + | + |
| 12 | + | + | − | − |
| 13 | + | + | − | − |
| 14 | + | + | − | − |
| 15 | + | + | − | − |
| 16 | + | + | − | − |
| 17 | + | + | − | − |
| 18 | + | + | − | − |
| 19 | + | + | − | − |

EXAMPLE 7

Alternate Assay Procedures for Use of Monoclonal Antibodies 31-42-19 and 31-90-25

A. Monoclonal antibody 31-42-19

As decribed in Example 6, the assay configuration designed specifically for capture of HIV-I detects as low as 800 pg/ml of HIV-2 p24 due to a high degree of cross reactivity observed between the core antigens of HIV-I and HIV-2. Based on these findings, monoclonal antibody 31-42-19 can be successfully used in the design of a highly sensitive HIV-2 p24 antigen assay. In addition, an antibody can be generated against native protein, synthetic peptide or recombinant protein including both HIV-I and HIV-2 p24 epitopes. Such an antibody either on solid phase or in solution as a probe, with monoclonal antibody 31-42-19 as probe or on solid phase, respectively, can also be used to design an immunoassay that would detect both HIV-I and HIV-2 p24 with equal efficiency. Thus, monoclonal antibody 31-42-19 can be employed in assays that detect both HIV-I and HIV-2 or assays that discriminate HIV-I and HIV-2 when used in appropriate enzyme immunoassay configurations.

B. Monoclonal Antibody 31-90-25

In another embodiment of the invention, monoclonal antibody 31-90-25 can be employed as a labelled probe for the detection of anti-HIV-I core antibodies in biological samples. Labelling can be performed using horseradish peroxidase. Briefly, the HRPO was activated by addition of 1.6 ml of 5 mg/ml HRPO (Sigma) to 1.6 ml of NaIO$_4$ at 17 mg/ml. The mixture was incubated 30 min in the dark followed by G25 Sephadex gel filtration. Fractions containing activated HRPO were pooled and protein concentration was adjusted to approximately to 0.6 mg/ml. One ml of 1 mg/ml 31-90-25 lgG previously dialysed into 50 mM Na$_2$CO$_3$ buffer, pH9.5, was added to 1.1 ml of activated HRPO at 30° C. and incubated for 2 hr in the dark, followed by a 30 minute incubation at 4° C. The theoretical coupling ratio of HRPO:lgG in the reaction mixture was 4:1. Freshly prepared Na$_2$BH$_4$ (0.08 ml of 5 mg/ml solution in cold 10 mM Na$_2$CO$_3$, pH 9.5) was added to the mixture and left overnight at 4° C., followed by addition of 0.08 ml acetone which was allowed to react for 30 min at 30° C. Finally, 7.7 ml of 1.43% bovine serum albumin in PBS (pH 7.2) were added to yield a final IgG concentration of 100 μg/ml; aliquots were stored at −70° C. An appropriate dilution of this conjugated antibody was made in a suitable diluent and employed in the assay described below.

First, a test sample, presumably containing anti-HIV-I p24, was mixed with partially purified recombinant p24 (see Example 1), and then incubated. Next, the mixture was incubated with a bead, previously coated with anti-HIV-I p24 antibody purified from sera of HIV-I seropositive individuals, and [HRPO]31-90-25 simultaneously. The absence of bound recombinant p24 resulted in a reduction of O.D. values at 492 nm and indicated the presence of anti-HIV-I p24 antibodies in the test sample.

To determine specificity of the assay, a population of blood donors having no known risk factors for exposure to HIV-I were tested in the assay. The data were compared with that of an assay, which employs a polyclonal human anti-HIV-I IgG as a probe, of established clinical efficacy (ENVACOR assay, Abbott Laboratories, North Chicago, Ill.). Data from both assays were in complete agreement. Out of 160 samples tested by both assays, all of them were negative for antibodies to HIV-I p24 (as well as negative for antibodies to HIV-I gp41 tested by the ENVACOR assay).

In order to determine the sensitivity of the assay, eleven samples from persons known to have antibodies to HIV-I by Western Blot or other HIV-I detection assays, were serially diluted in NHP. Samples from each of these dilutions were tested by the above-mentioned assays and results were compared. The results, described in Table 10, clearly indicate that the monoclonal probe assay showed significantly higher endpoint titers than the ENVACOR assay. This clearly illustrates superior sensitivity of the monoclonal assay.

TABLE 10

Sensitivity of Monoclonal Probe Immunoassay for Detection of HIV-I anti-p24 Antibodies.

| Patient | Diagnosis | Endpoint Titers[a] ENVACOR | Monoclonal |
|---|---|---|---|
| 1 | AIDS | neg[b] | neg |
| 2 | AIDS | ND[c] | neg |
| 3 | AIDS | ND | ND |
| 4 | AIDS | ND | 32 |
| 5 | AIDS | 64 | 1024 |
| 6 | ARC | ND | 2 |
| 7 | ARC | ND | 2 |
| 8 | ARC | ND | 4096 |
| 9 | ASYM | 4096 | 8192 |
| 10 | ASYM | 65,536 | 1,048,576 |
| 11 | ASYM | ND | 512 |

[a]Reciprocal of endpoint dilutions are given. End point dilutions defined as highest dilution of patient sera exhibiting positive results for antibodies to HIV-I p24.
[b]neg-negative for antibodies to HIV-I p24
[c]ND-not determinable (antibody titers may be too low to be detected by the assay)

The foregoing disclosure and experiments described herein set forth preferred assay configurations, but this is for illustrative purposes only and is not intended in any way to limit the scope of this invention. In addition, one skilled in the art will appreciate that the above-described monoclonal antibodies can be used for the detection of native HIV-I p24 or recombinant-derived HIV-I p24 in various assay formats under varied conditions of incubation, time and temperature to achieve optimum sensitivity and speed of the assay. Immunoassays within the scope of this invention include any assay format that is dependent upon the formation of an antigen/antibody complex, either in solution or on a solid phase, employing these antibodies individually or in a mixture.

What is claimed is:

1. An immunoassay for the detection of HIV-I p24 antigen in a test sample comprising forming an antibody/antigen complex wherein the antibody portion of said complex comprises a mixture of murine monoclonal antibodies, at least one monoclonal antibody of said mixture being capable of specifically binding to an epitope on HIV-I p24 to which epitope human anti-HIV-I p24 IgG does not competitively bind, and at least one other monoclonal antibody of said mixture being capable of binding to a different epitope of HIV-I p24 to which different epitope human anti-HIV-I p24 IgG competitively binds, and detecting the presence or amount in picogram sensitivity of the antibody/antigen complex formed.

2. The immunoassay of claim 1 wherein the presence or amount of the antibody/antigen complex formed is determined by incubating said complex with a labelled, anti-species antibody specific for said monoclonal antibodies.

3. The immunoassay of claim 2 wherein said label comprises a radioisotope, enzyme, fluorescent compound, chemiluminescent compound, or member of a specific binding pair.

4. The immunoassay of claim 1 wherein the antibody which binds to the epitope on HIV-1 p24 to which epitope human anti-HIV-1 p24 IgG does not competitively bind is monoclonal antibody 31-42-19 and the antibody which binds to the different epitope to which different epitope human anti-HIV-1 p24 IgG competitively binds is monoclonal antibody 31-90-25.

5. The immunoassay of claim 4 wherein said monoclonal antibodies 31-42-19 and 31-90-25 are in solution.

6. The immunoassay of claim 4 wherein said monoclonal antibodies 31-42-19 and 31-90-25 are coated on a solid support.

7. The immunoassay of claim 5 wherein said antibody portion of said complex further comprises human anti-HIV-I IgG coated on a solid support.

8. The immunoassay of claim 6 wherein said antibody portion of said complex further comprises an anti-HIV-I antibody or a fragment thereof.

9. The immunoassay of claim 8 wherein said antibody portion of said complex further comprises anti-HIV-I F(ab')$_2$.

10. The immunoassay of claim 9 wherein said antibody portion of said complex further comprises anti-HIV-I p24 F(ab')$_2$.

11. A diagnostic reagent for detection of HIV-1 p24 antigen or HIV-2 p24 antigen comprising a monoclonal antibody which specifically binds to an epitope on HIV-1 p24 to which epitope human anti-HIV-1 p24 IgG does not competitively bind and which monoclonal antibody also specifically binds to HIV-2 p24.

12. An immunoassay for the detection of HIV-1 p24 antigen in a human test sample comprising:
   a. contacting a human test sample with a solid support coated with human anti-HIV-1 IgG for a time and under conditions sufficient to form antibody/antigen complexes;
   b. contacting said complexes with a murine monoclonal antibody mixture comprising monoclonal antibodies 31-42-19 secreted by ATCC HB 9726 and 31-90-25 secreted by ATCC HB 9725 for a time and under conditions sufficient to form antibody/antigen/antibody complexes;

c. contacting said antibody/antigen/antibody complexes with an anti-mouse antibody or fragment thereof conjugated to a detectable label capable of generating a measurable signal;

d. measuring the signal generated to determine the presence of HIV-1 p24 in picogram sensitivity in the test sample.

13. The immunoassay of claim 12 wherein said solid support is simultaneously contacted with said human test sample and said mouse monoclonal antibody mixture.

14. An immunoassay for detection of the presence or amount of HIV-2 p24 antigen in a human test sample, comprising forming an antibody/antigen complex wherein the antibody portion of said complex comprises a monoclonal antibody capable of specifically binding to an epitope on HIV-1 p24 to which epitope human anti-HIV-1 p24 IgG does not competitively bind and which monoclonal antibody also specifically binds to HIV-2 p24, and detecting the presence or amount of the antibody/antigen complex formed.

15. A diagnostic kit for the detection of HIV-1 p24 antigen comprising:

a container containing a mixture of at least two murine monoclonal antibodies wherein at least one monoclonal antibody of said mixture specifically binds to an epitope on HIV-1 p24 to which epitope human anti-HIV-1 p24 IgG does not competitively bind and wherein at least one other monoclonal antibody of said mixture specifically binds to a different epitope of HIV-1 p24 to which different epitope human anti-HIV-1 p24 IgG competitively binds.

16. The diagnostic kit of claim 15 wherein said murine monoclonal antibody which specifically binds to an epitope on HIV-1 p24 to which epitope human anti-HIV-1 p24 IgG does not competitively bind is designated as monoclonal antibody 31-42-19 secreted by the hybridoma cell line ATCC 9726 and wherein said monoclonal antibody which is capable of binding to a different epitope of HIV-1 p24 to which different epitope human anti-HIV-1 p24 IgG competitively binds is designated as the 31-90-25 monoclonal antibody secreted by the hybridoma cell line ATCC HB 9725.

17. The immunoassay of claim 12 wherein said solid support is selected from the group consisting of wells of reaction trays, test tubes, polystyrene beads, strips, membranes and microparticles.

18. The immunoassay of claim 12 wherein said label is selected from the group consisting of enzymes, radioisotopes, fluorescent compounds and chemiluminescent compounds.

19. The immunoassay of claim 18 wherein said enzymatic label is horseradish peroxidase.

20. The immunoassay of claim 12, 18 or 19 further comprising a hapten and labelled anti-hapten system wherein the hapten is conjugated to the labeled murine monoclonal antibody.

21. The diagnostic reagent of claim 20 wherein said monoclonal antibody is the monoclonal antibody secreted by the hybridoma cell line A.T.C.C. HB 9726.

* * * * *